(12) United States Patent
Sakano et al.

(10) Patent No.: US 8,247,078 B2
(45) Date of Patent: Aug. 21, 2012

(54) FLUORINE-CONTAINING ACRYLATE

(75) Inventors: Yasunori Sakano, Annaka (JP); Noriyuki Koike, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 423 days.

(21) Appl. No.: 12/510,793

(22) Filed: Jul. 28, 2009

(65) Prior Publication Data

US 2010/0024685 A1    Feb. 4, 2010

(30) Foreign Application Priority Data

Jul. 29, 2008  (JP) ................................. 2008-195417
Dec. 11, 2008  (JP) ................................. 2008-315203

(51) Int. Cl.
*B32B 27/00* (2006.01)
*C08F 18/20* (2006.01)

(52) U.S. Cl. ........ 428/421; 428/447; 526/242; 526/245; 526/247; 526/248; 526/279; 522/172; 522/174

(58) Field of Classification Search .................. 526/242, 526/245, 247, 248; 556/419, 420
See application file for complete search history.

(56) References Cited

U.S. PATENT DOCUMENTS

| | | | | |
|---|---|---|---|---|
| 4,742,177 | A | * | 5/1988 | Yamamoto et al. ............ 556/419 |
| 5,374,702 | A | * | 12/1994 | Inomata et al. ................. 528/14 |
| 5,627,251 | A | * | 5/1997 | Sato et al. ........................ 528/15 |
| 5,914,420 | A | * | 6/1999 | Buese et al. .................... 556/448 |
| 6,160,148 | A | * | 12/2000 | Dauth et al. .................... 556/419 |
| 7,781,604 | B2 | * | 8/2010 | Sakano et al. ................. 556/406 |

FOREIGN PATENT DOCUMENTS

| | | |
|---|---|---|
| EP | 0320537 B1 | 6/1989 |
| JP | 5-194322 A | 8/1993 |
| JP | 11-349651 A | 12/1999 |

OTHER PUBLICATIONS

European Search Report dated Jan. 19, 2010 issued in corresponding European Application No. 09166582.8.

Kobunshi Ronbunshu, vol. 64, No. 4, pp. 181-190 (Apr. 2007).

* cited by examiner

*Primary Examiner* — Mark Eashoo
*Assistant Examiner* — Nicole M Buie-Hatcher
(74) *Attorney, Agent, or Firm* — Birch, Stewart, Kolasch & Birch, LLP

(57) ABSTRACT

Photocurable fluorine compound, compatible with non-fluorine organic compounds, of formula (1),

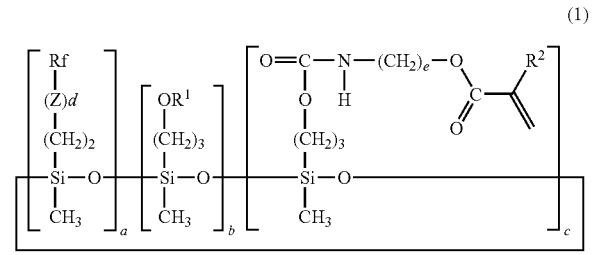

(1)

wherein: a is 1-4, b is 0-3, c is 1-4, provided that a+b+c is 3-5; e is 2-8; $R^1$ has formula (2), $$(C_4H_8O)_f(C_3H_6O)_g(C_2H_4O)_h(CH_2O)_iR^3 \qquad (2)$$

wherein f, g, h, and i are independently 0-100, and $R^1$ has an MW of 30-3000, these repeating units may be sequenced at random, and $R^3$ is $C_{1-10}$ hydrocarbon; $R^2$ is independently H, F, $CH_3$, or $CF_3$; Rf is a perfluoropolyether residue represented by the following formula (3),

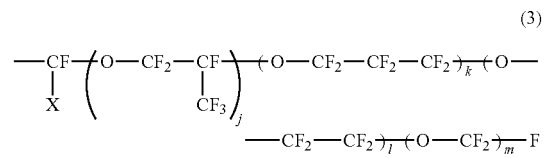

(3)

wherein j, k, l, and m are independently of each other integers of 0 to 50, provided that a molecular weight of Rf is in a range of 200 to 6000, X is F or $CF_3$, and these repeating units may be sequenced at random; Z is a divalent organic group; and d is 0 or 1.

9 Claims, No Drawings

FLUORINE-CONTAINING ACRYLATE

REFERENCE TO RELATED APPLICATION

This application claims the benefits of Japanese Patent Application No. 2008-315203 filed on Dec. 11, 2008, the contents of which are hereby incorporated by reference.

FIELD OF THE INVENTION

The present invention relates to a photo-curable fluorine-containing acrylate, particularly to a fluorine-containing acrylate or alpha-substituted, fluorine-containing acrylate which has a cyclosiloxane structure and good compatibility with non-fluorine solvents. Both of the fluorine-containing acrylate and the alpha-substituted, fluorine-containing acrylate are hereinafter collectively referred to as "a fluorine-containing acrylate".

BACKGROUND OF THE INVENTION

Conventionally, polymerizable monomers which have a perfluoroalkyl group in a side chain, such as fluorine-containing alkyl ester of acrylic acid and a fluorine-containing alkyl ester of methacrylic acid, are widely known as a fluorine compound which can be cured by radiation of light, such as ultraviolet ray. As a typical example, acrylate which has the following structure has widely been used in order to provide a substrate surface with water- and oil-repellency, stain resistance, abrasion resistance, and scratch resistance.

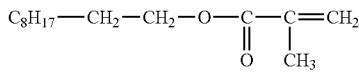

However, recently, there is an increasing tendency with environmental concerns to regulate use of compounds which have a long-chain perfluoroalkyl group having eight or more carbon atoms. Meanwhile, it is known that acrylic compounds having a perfluoroalkyl group with less than eight carbon atoms give worse surface property than ones having a perfluoroalkyl group with eight or more carbon atoms do (non-patent literature 1).

Meanwhile, photo-curable fluorine compounds are known which have a perfluoropolyether group composed of an oxygen atom participating in an ether bond and a perfluoroalkyl group having three or less adjoining carbon atoms. For instance, patent literature 1 discloses the following acrylic compound which is derived from a hexafluoropropylene oxide oligomer.

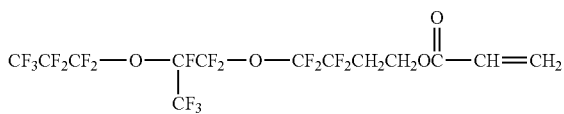

Patent literature 2 discloses a urethane acrylate which is a reaction product of a fluorine-containing polyether diol with 2-isocyanatoethyl methacrylate. However, this fluorine compound has bad compatibility with photo polymerization initiators, non-fluorinated acrylates, and non-fluorinated organic solvents due to its water- and oil-repellency and, therefore, can be blended with restricted number of components and has restricted usage.

[Non-patent literature 1]: Koubunshi Ronbun-Shu Vol. 64, No. 4, pp 181-190 (April, 2007).
[Patent literature 1]: Japanese Patent Application Laid-Open No. Hei-5-194322
[Patent literature 2]: Japanese Patent Application Laid-Open No. Hei-11-349651

DISCLOSURE OF THE INVENTION

Problems to be Solved by the Invention

The purpose of the present invention is to provide a photo curable fluorine compound which has good compatibility with non-fluorine organic compounds, maintaining good properties as a fluorine compound.

Means to Solve the Problems

Namely, the present invention is the following fluorine-containing acrylate or alpha-substituted, fluorine-containing acrylate represented by the following formula (1),

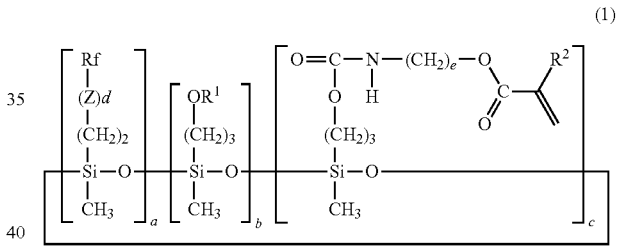

wherein a is an integer of from 1 to 4, b is an integer of from 0 to 3, and c is an integer of from 1 to 4, provided that a+b+c is 3, 4, or 5;
e is an integer of from 2 to 8;
$R^1$ is a group represented by the following formula (2),

$$—(C_4H_8O)_f(C_3H_6O)_g(C_2H_4O)_h(CH_2O)_iR^3 \quad (2)$$

wherein f, g, h, and i are, independently of each other, an integer of from 0 to 100, provided that a molecular weight of $R^1$ is in a range of 30 to 3000,
these repeating units may be sequenced at random, and
$R^3$ is a saturated or unsaturated hydrocarbon group having 1 to 10 carbon atoms;
$R^2$ is, independently of each other, a hydrogen atom, a fluorine atom, a methyl group, or a trifluoromethyl group;
Rf is a perfluoropolyether residue represented by the following formula (3),

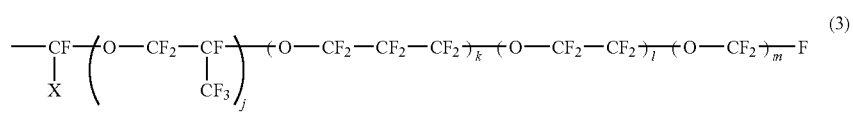

wherein j, k, l, and m are, independently of each other, an integer of from 0 to 50, provided that a molecular weight of Rf is in a range of 200 to 6000, X is a fluorine atom or a trifluoromethyl group, and these repeating units may be sequenced at random;

Z is a divalent organic group; and d is 0 or 1.

Effects of the Invention

The present fluorine-containing acrylate is good in compatibility with non-fluorinated organic compounds and, further, can be cured by light to form a cured product which is water- and oil-repellent. Accordingly, the present acrylate is useful as an additive for a hard coat.

BEST EMBODIMENTS TO WORK THE INVENTION

The present fluorine-containing acrylate is represented by the following formula (1).

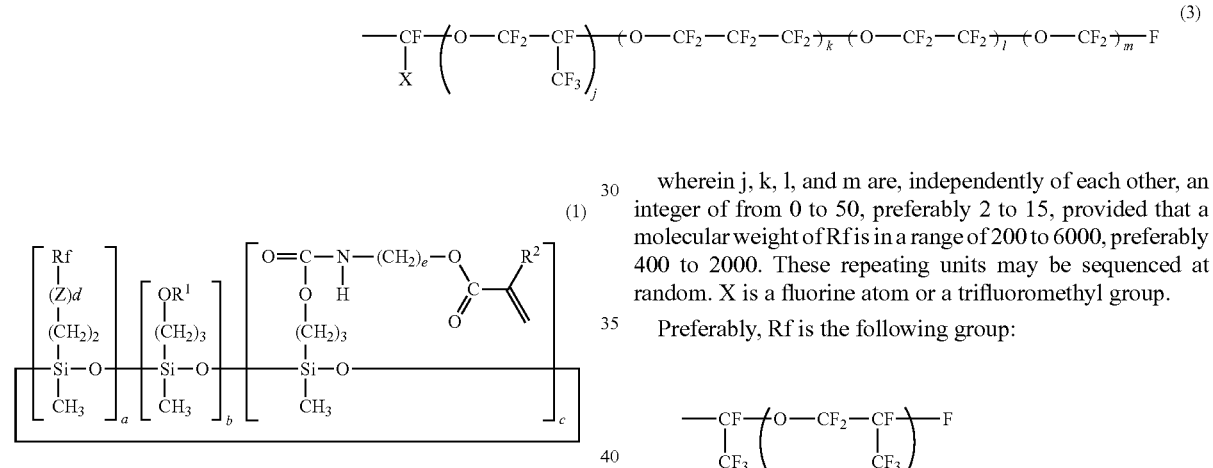

In formula (1), a is an integer of from 1 to 4, b is an integer of from 0 to 3, and c is an integer of from 1 to 4, provided that a+b+c is 3, 4, or 5. Preferably, a is 1, b is 1 or 2, and c is 1 or 2. As described below, the afore-mentioned acrylate is prepared by reacting a hydrogen atom bonded to Si with an unsaturated group in a compound which is to form a side chain and, therefore, the amount of the side chain can be changed by changing a ratio of the compound used. A mixture of the compounds having different amounts of the side chain can also be prepared. For instance, a mixture of 50 mole % of a compound with a=b=c=1 with 50 mole % of a compound with a=1 and b=c=2 can be prepared, so that a compound with a=1 and b=c=1.5 as a whole is obtained.

e is an integer of from 2 to 8, preferably, 2 to 4.

$R^1$ is a group represented by the following formula (2),

—($C_4H_8O$)$_f$($C_3H_6O$)$_g$($C_2H_4O$)$_h$($CH_2O$)$_i$$R^3$     (2)

wherein f, g, h, and i are, independently of each other, an integer of from 0 to 100, preferably 1 to 20, provided that a molecular weight of $R^1$ is in a range of 30 to 3000, preferably 100 to 1000. The oxyalkylene repeating units may be sequenced at random.

$R^3$ is a saturated or unsaturated hydrocarbon group having 1 to 10 carbon atoms, such as a methyl group, an ethyl group, a propyl group, an isopropyl group, a butyl group, a pentyl group, a hexyl group, a 2-ethylhexyl group, a cyclohexyl group, a phenyl group, and a benzyl group, preferably, a methyl group and an ethyl group.

As a preferred example of $R^1$, mention may be made of the following,

—($C_2H_4O$)$_n$$CH_3$ wherein n is an integer of from 1 to 100.

More preferably, mention may be made of the following,

—($C_2H_4O$)$_p$$CH_3$

—($C_3H_6O$)$_p$$CH_3$ wherein p is an integer of from 2 to 10 and the propylene group may be branched.

$R^2$ is, independently of each other, a hydrogen atom, a fluorine atom, a methyl group, or a trifluoromethyl group, preferably a hydrogen atom.

Rf is a perfluoropolyether residue represented by the following general formula (3),

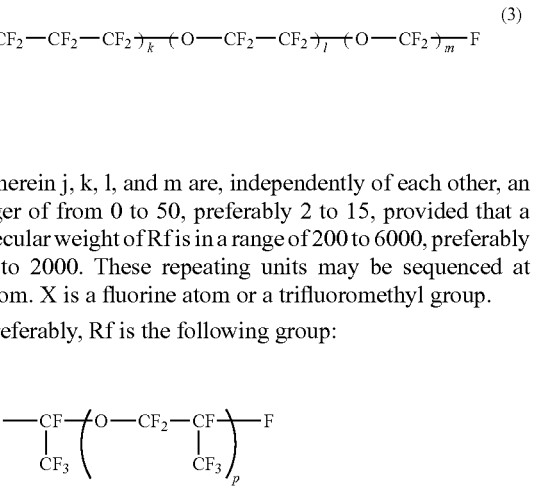

wherein j, k, l, and m are, independently of each other, an integer of from 0 to 50, preferably 2 to 15, provided that a molecular weight of Rf is in a range of 200 to 6000, preferably 400 to 2000. These repeating units may be sequenced at random. X is a fluorine atom or a trifluoromethyl group.

Preferably, Rf is the following group:

wherein p is an integer of from 1 to 30, preferably 2 to 15, particularly 3 to 10.

In formula (1), Z is a divalent organic group. The structure of Z is not particularly limited as far as Z can link Rf to an ethylene group and does not inhibit the polymerization of the acryl group. For instance, mention may be made of the following groups.

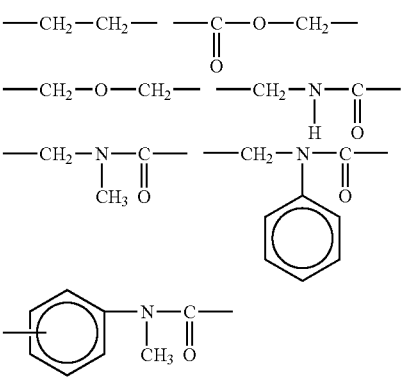

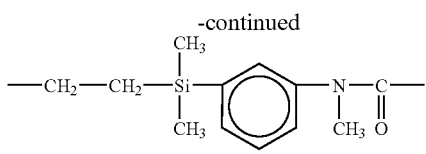

Among these, the following group is particularly preferred.

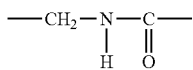

The afore-mentioned fluorine-containing acrylate can be prepared in the following process.

First, the following is subjected to addition reaction in the presence of a known catalyst comprising a metal of the platinum group: a cyclic hydrogensiloxane represented by the following formula (4),

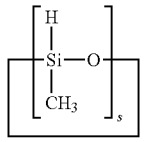

(s = 3, 4, 5)

the following fluorine-containing olefin compound (5),

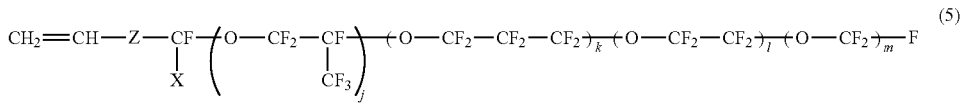

wherein X, j, k, l, and m are as defined above, a polyether compound having an allyl group on one end (6), $$CH_2=CH-CH_2-O-(C_4H_8O)_f(C_3H_6O)_g(C_2H_4O)_h(CH_2O)_iR^3 \quad (6)$$

wherein f, g, h and i are as defined above, and allyl alcohol, to form a compound represented by the following formula (7).

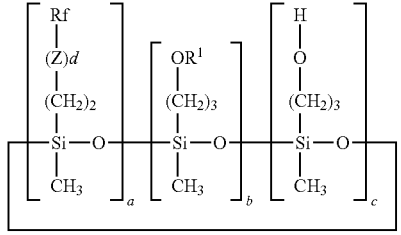

An OH group in the afore-mentioned (7) is reacted with the following compound (8)

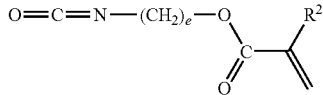

to obtain the compound having the structure of the afore-mentioned formula (1).

In the addition reaction of (5), (6), and the allyl alcohol with compound (4), the order of the reaction is not limited to any particular one. Preferably, (5) and (6) are addition reacted with (4) and, then, a largely excess amount of the allyl alcohol relative to unreacted Si—H group is applied, in order to avoid condensation between the hydroxyl group and the Si—H group. Alternatively, (5) is first addition reacted with a largely excess amount of compound (4) unreacted (4) is removed for purification or an addition ratio of (5) to (4) is adjusted as desired by a separation means such as column chromatography; and, then, the addition reaction of (6) and that of the allyl alcohol are carried out, so that the average addition ratio of each component can be controlled stricter.

The reaction between compounds (7) and (8) may proceed by blending the both compounds under mild conditions between 0 and 70 degrees C. The reaction rate may be accelerated by adding 0.001 to 2% by weight, preferably 0.001 to 0.5% by weight, of a suitable catalyst system, relative to the total reactants weight. Examples of the suitable catalyst system include tin derivatives such as tin acetate, dibutyltin dilaurate, dibutyltin dioctate, dibutyltin diacetate, dioctyltin dilaurate, dioctyltin dioctate, dioctyltin diacetate, and stannous dioctanoate; iron derivatives such as iron acetylacetonate; titanium alcolate such as titanium tetraisopropylate; and tertiary amine such as triethylamine, and N-methylmorpholine. If desired, the reaction may be carried out under dilution with various kinds of solvents.

The resulting compound of the present invention can be blended in a non-fluorine type of a hard coat composition to provide a hard coat layer with stain resistance, fingerprint proof property, water repellency, and oil repellency. Any of non-fluorine type of hard coat composition may be used as far as the composition can be blended with the present compound and cured.

A preferable hard coat composition comprises urethane acrylate as a major component. Examples of the urethane acrylate include a reaction product of a polyisocyanate with a (meth)acrylate having a hydroxyl group; a reaction product of a polyisocyanate and a polyester having terminal diols with a (meth)acrylate having a hydroxyl group; and a reaction product obtained by reacting a polyisocyanate, which is obtained by reacting a polyol with an excess amount of a diisocyanate, with a (meth)acrylate having a hydroxyl group. Inter alia, the present compound is preferably blended in a composition comprising a urethane acrylate which is a reaction product of a (meth)acrylate having a hydroxyl group selected from 2-hydroxyethyl(meth)acrylate, 2-hydroxy-3-acryloyloxypropylmethacrylate, and pentaerythritol triacrylate with a polyisocyanate selected from hexamethylene diisocyanate, isophorone diisocyanate, trilene diisocyanate, and diphenylmethane diisocyanate.

Examples of the other hard coat compositions which are suitable for the present compounds to be blended in include one whose major component comprises (meth)acrylic compounds having 2 to 6 functional groups such as 1,6-hexanediol di(meth)acrylate, neopentyl glycol di(meth)acrylate, ethylene glycol di(meth)acrylate, ethylene oxide isocyanurate-modified di(meth)acrylate, EO-isocyanurate modified tri (meth)acrylate, trimethylolpropane tri(meth)acrylate, pentaerythritol tri(meth)acrylate, glycerol tri(meth)acrylate, tris(meth)acrylolyoxyethyl phosphate, (2,2,2-tri-(meth)acryloyloxymethyl)ethyl hydrogen phthalate, glycerol tri(meth)acrylate, pentaerythritol tetra(meth)acrylate, ditrimethylolpropane tetra(meth)acrylate, dipentaerythritol penta(meth)acrylate, dipentaerythritol hexa(meth)acrylate, and sorbitol hexa(meth)acrylate; epoxyacrylates obtained by addition reaction of the afore-mentioned (meth)acrylic compounds with ethylene oxide, propylene oxide, epichlorohydrin, or an aliphatic acid-, alkyl-urethane-modified epoxy resin; and acrylate ester copolymers which have a (meth)acryloyl group in their side chain.

Various hard coat materials which can be cured with active energy ray, such as ultraviolet ray or electron beam, are commercially available from various companies. For instance, mention may be made of various trade names, such as "Beam Set" from Arakawa Chemical Industries Ltd.; "Ubiq" from Oohashi Chemical Industries Ltd.; "UV coat" from Origin Electric Co., Ltd.; "Cashew UV" from Cashew Co., Ltd.; "DeSolite" from JSR Corporation; "Seika Beam" from Dainichiseika Chemical Industries Co., Ltd.; "Shikoh" from The Nippon Synthetic Chemical Industry Co., Ltd.; "Fujihard" from Fujikura Kasei Co., Ltd.; "Diabeam" from Mitsubisi Rayon Co., Ltd.; and "Ultra Vin" from Musashi Paint Co., Ltd. The present compound can also be blended in a fluorinated type of a hard coat composition to increase, for instance, water repellency and oil repellency.

The present compound is blended in a hard coat composition and hardened to provide the coating with stain resistance, water repellency, oil repellency, and fingerprint proof property or to enhance such properties. The coating is resistant against fat of human being such as fingerprint, sebum and sweat, and cosmetics. Even when stain attaches to the coating, the stain is easily wiped off. Accordingly, the present compound can be used as an additive for curable compositions which are to be coated on a surface of articles, which surface may be touched by a human body and fouled with human fat or cosmetics, to form a coating film or protective film thereon. Examples of the articles include optical recording media such as optical discs and hologram records, for instance, optical magnetic discs, CD's, LD's, DVD's, and blue ray discs; optical parts and optical devices such as lenses of glasses, prisms, lens sheet, pellicle films, polarizing plates, optical filters, lenticular lenses, Fresnel lenses, antireflection films, optical fibers, and optical couplers; screens or displaying devices such as CRT's, liquid crystal displays, plasma displays, electroluminescence displays, rear projection displays, fluorescent display tubes (VFD's), field emission projection displays and toner displays, particularly, image-displaying devices such as personal computers, mobile phones, personal digital assistants, game machines, digital cameras, digital camcorders, automated teller machines, cash dispensers, automatic vending machines, navigation devices of, for instance, automobiles, and security system terminals, and devices for displaying and inputting an image of touchpanel type with which the operation thereof is also carried out, such as touch sensors and touchscreens; inputting devices such as mobile phones, personal digital assistants, mobile music players, and handheld game machines, remote controllers, controllers, key boards and panel switches for in-car-devices; surfaces of housing of mobile phones, personal digital assistants, cameras, mobile music players, and handheld game machines; coatings and surfaces of exteriors of automobiles, pianos, classy furniture, and marble stones; parts made of transparent glass or plastic (acryls or polycarbonates) and various mirror members such as protective glass for exhibiting works of art, show windows, show cases, covers for advertisement, covers for photo stands, wrist watches, windshields for automobiles, window glass for trains and air planes, headlights and tail lamps of automobiles. The amount to be added is properly adjusted in a range of from 0.1 part by weight to 10 parts by weight relative to 100 parts by weight of a solid content of a hard coat composition, depending on desired oil repellency, solubility of the composition and curing conditions.

EXAMPLES

The present invention will be specifically explained by the following Examples but shall not be limited thereto.

Example 1

In a 100 ml three-necked flask equipped with a reflux device and a stirrer were placed 50.0 g of the fluorine-containing cyclosiloxane represented by the following formula (9),

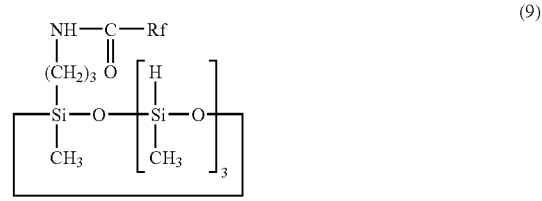

wherein Rf is the following group,

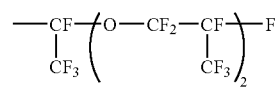

and 20.0 g of toluene under a dry nitrogen atmosphere and heated with stirring up to 90 degrees C. Then, a mixture solution of 24.8 g of polyoxyethylenemethyl allyl ether represented by the following formula (10), $$CH_2=CH-CH_2-O-(CH_2CH_2O)_{4.5}CH_3 \qquad (10)$$

wherein the length of the polyoxyethylene chain has distribution and the average length is 4.5, with 0.0180 g of a solution of vinylsiloxane-modified chloroplatinic acid in toluene (platinum content: $4.48 \times 10^{-8}$ mole) was added dropwise over one hour and stirred at 90 degrees C. for 12 hours.

In another 100 ml three-necked flask equipped with a reflux device and a stirrer was placed 19.6 g of allyl alcohol and heated to 90 degrees C. under a dry nitrogen atmosphere. Then, the afore-mentioned reaction solution, which had been cooled down to room temperature, was added dropwise over 3 hours and stirred at 90 degrees C. for 16 hours. The obtained reaction solution was treated at 100 degrees C. and 6 Torr for 2 hours to remove the unreacted allyl alcohol.

To 60 g of the compound obtained, 10 g of 2-isocyanatoethyl acrylate and 0.01 g of dioctyltin laurate were added under a dry air atmosphere and stirred at 25 degrees C. for 12 hours to obtain the compound having the following average composition. The chemical shifts in the $^1$H-NMR and $^{19}$F-NMR spectra of the compound are as shown below.

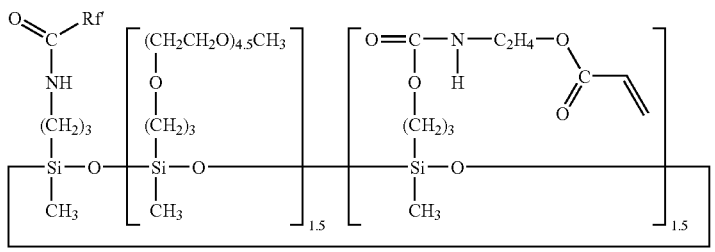

wherein Rf is as defined above.

Chemical shifts in $^1$H-NMR spectrum (Measuring device: JMN-LA300W from JEOL, solvent: CDCl$_3$)

| Shift (TMS reference) | |
|---|---|
| 0~0.2 ppm | —Si—C$\underline{H}_3$ 12H |
| 0.4~0.6 ppm | —Si—C$\underline{H}_2$—CH$_2$— 8H |
| 1.5~1.7 ppm | —Si—CH$_2$—C$\underline{H}_2$—CH$_2$—O— 6H |
| | —Si—CH$_2$—C$\underline{H}_2$—CH$_2$—NH— 2H |
| 2.2~2.3 ppm | —CF(CF$_3$)—CO—N$\underline{H}$— 1H |
| 3.3~3.7 ppm | —Si—CH$_2$—CH$_2$—C$\underline{H}_2$—O—CH$_2$— 3H |
| | —Si—CH$_2$—CH$_2$—C$\underline{H}_2$—NH— 2H |
| | —NH—C$\underline{H}_2$—CH$_2$—O— 3H |
| | —Si—CH$_2$—CH$_2$—CH$_2$—O—(C$_2$H$_4$O)$_{4.5}$—C$\underline{H}_3$ 31.5H |
| 4.0~4.1 ppm | —Si—CH$_2$—CH$_2$—C$\underline{H}_2$—O—CONH— 3H |
| 4.2~4.3 ppm | —NH—CH$_2$—C$\underline{H}_2$—O— 3H |
| 4.8~5.4 ppm | —Si—CH$_2$—CH$_2$—CH$_2$—O—CON$\underline{H}$— 1.5H |
| 5.8~6.4 ppm | —C$\underline{H}$=C$\underline{H}_2$ 4.5H |

Chemical shifts in $^{19}$F-NMR

| Shift (F-11 reference) | |
|---|---|
| −145.6 ppm | CF$_3$CF$_2$CF$_2$—O—C$\underline{F}$(CF$_3$)CF$_2$—O—CF(CF$_3$)—CO—NH— 1F |
| −132.7 ppm | —C$\underline{F}$(CF$_3$)—CO—NH— 1F |
| −130 ppm | CF$_3$C$\underline{F}_2$CF$_2$—O— 2F |
| −86~−79 ppm | C$\underline{F}_3$CF$_2$C$\underline{F}_2$—O—CF(C$\underline{F}_3$)C$\underline{F}_2$—O—CF(C$\underline{F}_3$)—CO—NH— 13F |

Example 2

In a 100 ml three-necked flask equipped with a reflux device and a stirrer were placed 50.0 g of the fluorine-containing cyclosiloxane represented by the following formula (11),

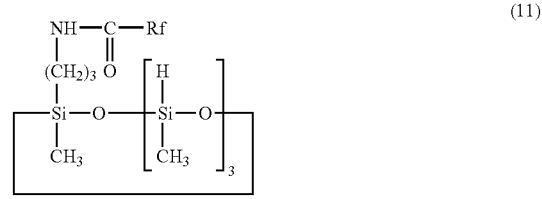

(11)

wherein Rf is the following group, the number of the repeating unit has distribution and the average number of the repeating unit is 5.2,

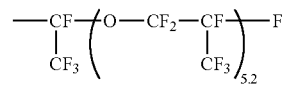

and 20.0 g of toluene under a dry nitrogen atmosphere, and heated with stirring up to 90 degrees C. Then, a mixture solution of 9.75 g of polyoxyethylenemethyl allyl ether represented by the above-mentioned formula (10) with 0.0110 g of a solution of vinylsiloxane-modified chloroplatinic acid in toluene (platinum content: 2.73×10$^{-8}$ mole) was added dropwise over 1 hour and stirred at 90 degrees C. for 12 hours.

In another 100 ml three-necked flask equipped with a reflux device and a stirrer was placed 16.9 g of allyl alcohol and heated to 90 degrees C. under a dry nitrogen atmosphere. Then, the afore-mentioned reaction solution, which had been cooled down to room temperature, was added dropwise over 3 hours and stirred at 90 degrees C. for 16 hours. The obtained reaction solution was treated at 100 degrees C. and 6 Torr for 2 hours to remove the unreacted allyl alcohol.

To 60.0 g of the compound obtained, 7.01 g of 2-isocyanatoethyl acrylate and 0.010 g of dioctyltin laurate were added under a dry air atmosphere and stirred at 25 degrees C. for 12 hours to obtain the compound with the following average composition.

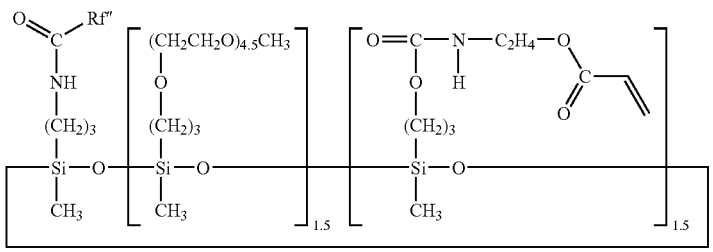

Chemical shifts in $^1$H-NMR spectrum (Measuring device: JMN-LA300W from JEOL, solvent: CDCl$_3$)

| Shift (TMS reference) | |
|---|---|
| 0~0.2 ppm | —Si—C$\underline{H}_3$ 12H |
| 0.4~0.6 ppm | —Si—C$\underline{H}_2$—CH$_2$— 8H |
| 1.5~1.7 ppm | —Si—CH$_2$—C$\underline{H}_2$—CH$_2$—O— 6H |
| | —Si—CH$_2$—C$\underline{H}_2$—CH$_2$—NH— 2H |
| 2.2~2.3 ppm | —CF(CF$_3$)—CO—N$\underline{H}$— 1H |
| 3.3~3.7 ppm | —Si—CH$_2$—CH$_2$—C$\underline{H}_2$—O—CH$_2$— 3H |
| | —Si—CH$_2$—CH$_2$—C$\underline{H}_2$—NH— 2H |
| | —NH—C$\underline{H}_2$—CH$_2$—O— 3H |
| | —Si—CH$_2$—CH$_2$—CH$_2$—O—(C$_2$H$_4$O)$_{4.5}$—C$\underline{H}_3$ 31.5H |
| 4.0~4.1 ppm | —Si—CH$_2$—CH$_2$—C$\underline{H}_2$—O—CONH— 3H |
| 4.2~4.3 ppm | —NH—CH$_2$—C$\underline{H}_2$—O— 3H |
| 4.8~5.4 ppm | —Si—CH$_2$—CH$_2$—CH$_2$—O—CON$\underline{H}$— 1.5H |
| 5.8~6.4 ppm | —C$\underline{H}$=C$\underline{H}_2$ 4.5H |

Chemical shifts in $^{19}$F-NMR

| Shift (F-11 reference) | |
|---|---|
| −145.6 ppm | CF$_3$CF$_2$CF$_2$—O—[C$\underline{F}$(CF$_3$)CF$_2$—O]$_{4.2}$—CF(CF$_3$)—CO—NH— 4.2F |
| −132.7 ppm | —C$\underline{F}$(CF$_3$)—CO—NH— 1F |
| −130 ppm | CF$_3$C$\underline{F}_2$CF$_2$—O— 2F |
| −86~−79 ppm | C$\underline{F}_3$CF$_2$C$\underline{F}_2$—O—[CF(C$\underline{F}_3$)C$\underline{F}_2$—O]$_{4.2}$—CF(C$\underline{F}_3$)—CO—NH— 29F |

Comparative Example 1

In a 200 ml three-necked flask equipped with a reflux device and a mechanical stirrer were placed 15.5 g of 2-isocyanatoethyl methacrylate and 0.005 g of dioctyltin laurate under a dry air atmosphere. Then, 100 g of perfluoropolyether diol (from Solvay Solexis, trade name: FOMBLIN D 2000, average molecular weight: 2000) was added dropwise at 50 degrees C. over 1 hour. After the completion of the addition, the reaction mixture was stirred at 50 degrees C. for 5 hours. In the IR spectra of the reaction product, the peak at 2300 cm$^{-1}$ which is attributed to —N=C=O group disappeared. The perfluoropolyether diol which has methacryl groups at both ends was obtained.

Each 0.5 g of the compounds of Examples 1 and 2 and Comparative Example 1 was blended with 10 g of one of the different solvents described below to visually observe the solubility of each compound. The results are shown in Table 1, where + means that a transparent solution was obtained and − means that a transparent solution was not obtained.

TABLE 1

| Solvent | Example 1 | Example 2 | Comparative Example 1 |
|---|---|---|---|
| Methanol | + | + | − |
| Ethanol | + | + | − |
| THF | + | + | − |
| Ethyl acetate | + | + | − |
| Acetone | + | + | − |
| PGMEA | + | + | − |
| DMSO | − | − | − |
| HFCF-225 | + | + | + |

As seen in Table 1, the compounds of the Examples dissolve in more kinds of non-fluorinated solvents than conventional fluorine-containing acrylates do.

Evaluation on the Hard Coat Compositions

Each compound of Examples 1 and 2 was blended with a hard coat composition of a non-fluorine urethane acrylate type (Ultra Vin Clear, UV720KF, from Musashi Paint Co., Ltd.) and a thinner (Ultra Vin Clear Thinner Z 27095 from Musashi Paint Co., Ltd.) in the following ratio to prepare a solution thereof. As a blank, a solution which did not contain any additive was also prepared.

| | |
|---|---|
| Ultra Vin Clear UV720KF from Musashi Paint Co., Ltd. | 100 parts by mass |
| Ultra Vin Thinner Z 27095 from Musashi Paint Co., Ltd. | 100 parts by mass |
| Additive (Compound of Example 1 or 2) | 3 parts by mass |

Each solution was spin coated on a glass plate. It was irradiated with ultraviolet ray of 1.6 J/cm$^2$ in an ultraviolet irradiation device of a conveyer type to form a cured film. Each film was visually observed to evaluate its appearance. Water contact angles and oleic acid contact angles were measured on a contact angle meter from Kyowa Interface Science Co., Ltd. The compound of Comparative Example 1 could not be evaluated because its solubility was too bad to form a solution.

Table 2 shows the properties of the surfaces which were treated with each hard coat. Felt pen repellency was evaluated by drawing a line on the surface with an oil-based marking pen from Zebra Co., Ltd., High Macky, and visually observing how much its ink was repelled. A fingerprint wiping-off property was evaluated by pressing a forefinger on the surface to leave behind a fingerprint thereon, wiping the surface with tissue paper, and visually observing the wiping-off property.

TABLE 2

| Additive | None | Compound of Example 1 | Compound of Example 2 |
|---|---|---|---|
| Appearance | Transparent and colorless | Transparent and colorless | Transparent and colorless |
| Water contact angle in degrees | 91 | 97 | 107 |
| Oleic acid contact angle in degrees | 44 | 66 | 72 |
| Felt pen repellency | Not repelled | Repelled | Well repelled |
| Fingerprint wiping-off property | Difficult to wipe off | Easy to wipe off | Easy to wipe off |

INDUSTRIAL APPLICABILITY

As shown above, the present compound has good compatibility with non-fluorinated organic compounds and, therefore, can be used as an additive in compositions for surface hard coats of, for instance, glass, resins, films, paper, metals, ceramics, and wood; in compositions for surface protecting films of printed materials; and in painting composition.

The invention claimed is:
1. A fluorine-containing acrylate or alpha-substituted, fluorine-containing acrylate, represented by the following formula (1),

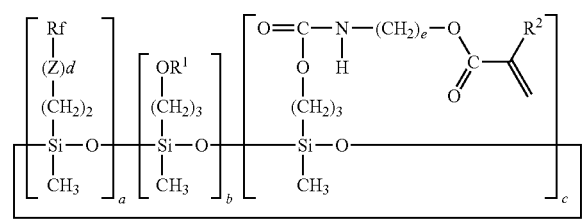
(1)

wherein
a is an integer of from 1 to 3, b is an integer of from 1 to 3, and c is an integer of from 1 to 3, provided that a+b+c is 3, 4, or 5;
e is an integer of from 2 to 8;
$R^1$ is a group represented by the following formula (2), $(C_4H_8O)_f(C_3H_6O)_g(C_2H_4O)_h(CH_2O)_iR^3$ (2)

wherein f, g, h, and i are, independently of each other, an integer of from 0 to 100, provided that a molecular weight of $R^1$ is in a range of 30 to 3000, these repeating units may be sequenced at random, and $R^3$ is a saturated or unsaturated hydrocarbon group having 1 to 10 carbon atoms;
$R^2$ is, independently of each other, a hydrogen atom, a fluorine atom, a methyl group, or a trifluoromethyl group;
Rf is a perfluoropolyether residue represented by the following formula (3)

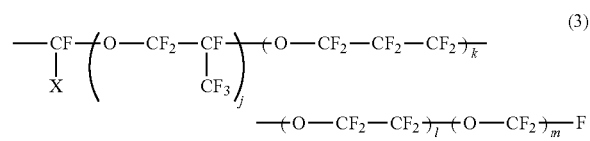
(3)

wherein j, k, l, and m are, independently of each other, an integer of from 0 to 50, provided that a molecular weight of Rf is in a range of 200 to 6000, X is a fluorine atom or a trifluoromethyl group, and these repeating units may be sequenced at random;
Z is a divalent organic group; and
d is 0 or 1.

2. The fluorine-containing acrylate or alpha-substituted, fluorine-containing acrylate according to claim 1, wherein $R^1$ in formula (1) is a group represented by either one of the following formulas, —(C$_2$H$_4$O)$_p$CH$_3$ —(C$_3$H$_6$O)$_p$CH$_3$ wherein p is an integer of from 2 to 10 and the propylene group may be branched.

3. The fluorine-containing acrylate or alpha-substituted, fluorine-containing acrylate according to claim 1 or 2, wherein Rf in formula (1) is a group represented by the following formula,

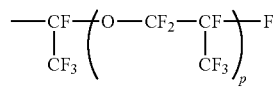

wherein p is an integer of from 1 to 30.

4. The fluorine-containing acrylate or alpha-substituted, fluorine-containing acrylate according to claim 1, wherein d in formula (1) is 1 and Z in formula (1) is a group represented by the following formula

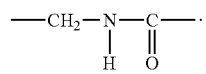

5. A composition obtained by blending the alpha-substituted, fluorine-containing acrylate or fluorine-containing acrylate according to claim 1 into a non-fluorine type of hard coat composition.

6. The composition according to claim 5, wherein the hard coat composition comprises a urethane acrylate as a major component.

7. The composition according to claim 5, wherein the hard coat composition comprises: (meth)acrylic compounds having 2 to 6 functional groups; epoxyacrylates obtained by addition reaction of the afore-mentioned (meth)acrylic compounds with ethylene oxide, propylene oxide, epichlorohydrin, or an aliphatic acid-, alkyl-urethane-modified epoxy resin; and acrylate ester copolymers which have a (meth)acryloyl group in their side chain.

8. The composition according to claim 5, wherein the hard coat composition comprises hard coat materials which can be cured with active energy ray.

9. A hard coating obtained by curing the composition according to any one of claims 5 to 8.

* * * * *